(12) United States Patent
Johnson et al.

(10) Patent No.: US 7,771,360 B2
(45) Date of Patent: Aug. 10, 2010

(54) BREAST SCANNING SYSTEM

(75) Inventors: Steven A. Johnson, Salt Lake City, UT (US); Michael Berggren, Salt Lake City, UT (US); David T. Borup, Salt Lake City, UT (US); Barry K. Hanover, Salt Lake City, UT (US); Rita Hanover, Salt Lake City, UT (US); Martin Kammeyer, Sandy, UT (US); Scott Olsen, Salt Lake City, UT (US); Jeffrey Pattee, Salt Lake City, UT (US); Frank L. Setinsek, Fruit Heights, UT (US); Kortlan D. Stewart, Salt Lake City, UT (US); James Wiskin, Salt Lake City, UT (US)

(73) Assignee: Techniscan, Inc., Salt Lake City, UT (US)

( * ) Notice: Subject to any disclaimer, the term of this patent is extended or adjusted under 35 U.S.C. 154(b) by 1889 days.

(21) Appl. No.: 10/821,407

(22) Filed: Apr. 8, 2004

(65) Prior Publication Data

US 2005/0143638 A1    Jun. 30, 2005

Related U.S. Application Data

(60) Provisional application No. 60/461,871, filed on Apr. 9, 2003.

(51) Int. Cl.
*A61B 8/00* (2006.01)

(52) U.S. Cl. .................................. 600/459; 600/437
(58) Field of Classification Search .............. 600/443, 600/437, 459
See application file for complete search history.

(56) References Cited

U.S. PATENT DOCUMENTS

| | | | | |
|---|---|---|---|---|
| 4,282,880 A | * | 8/1981 | Gardineer et al. | 600/437 |
| 4,298,009 A | * | 11/1981 | Mezrich et al. | 600/443 |
| 4,341,222 A | * | 7/1982 | Gardineer et al. | 600/437 |
| 4,662,222 A | * | 5/1987 | Johnson | 73/602 |
| 4,727,550 A | | 2/1988 | Chang et al. | |
| 4,798,209 A | | 1/1989 | Klingenback et al. | |
| 5,227,797 A | | 7/1993 | Murphy | |
| 5,588,032 A | * | 12/1996 | Johnson et al. | 378/8 |
| 5,677,893 A | | 10/1997 | De Hoop et al. | |

(Continued)

OTHER PUBLICATIONS

P.R. Williamson, "Tomographic inversion in reflection seismology," Geophys. J. Int. 100, pp. 255-274, 1990.

(Continued)

*Primary Examiner*—Long V Le
*Assistant Examiner*—Saurel J Selkin
(74) *Attorney, Agent, or Firm*—Thorpe North & Western, LLP

(57) ABSTRACT

A breast scanning system scans a breast of a patient with transducer arrays that transmit and receive ultrasound signals in a bath containing a medium, such as a liquid. A table is disposable over the bath to receive the patient thereon, and has an aperture formed in the table and positionable over the bath to receive the breast of the patient pendent therethrough and into the bath. The table is linearly vertically displaceable with respect to the bath. The system includes a preconditioning tank to precondition the liquid prior to being introduced into the bath. The bath includes means for securing the breast within the bath.

70 Claims, 10 Drawing Sheets

U.S. PATENT DOCUMENTS

| | | | | |
|---|---|---|---|---|
| 6,005,916 | A * | 12/1999 | Johnson et al. | 378/87 |
| 6,544,186 | B1 * | 4/2003 | Shelby et al. | 600/463 |
| 6,546,279 | B1 * | 4/2003 | Bova et al. | 600/429 |
| 6,587,540 | B1 * | 7/2003 | Johnson et al. | 378/62 |
| 6,636,584 | B2 * | 10/2003 | Johnson et al. | 600/437 |
| 6,782,759 | B2 * | 8/2004 | Shank et al. | 73/780 |
| 6,860,855 | B2 * | 3/2005 | Shelby et al. | 600/459 |
| 2003/0097066 | A1 * | 5/2003 | Shelby et al. | 600/443 |
| 2004/0064046 | A1 * | 4/2004 | Shehada | 600/437 |
| 2004/0082856 | A1 * | 4/2004 | Marmarelis | 600/437 |

OTHER PUBLICATIONS

W.W. Kim, D.T. Borup, S.A. Johnson, M.J. Berggren, and Y. Ahou, "Accelerated Inverse Scattering Algorithms for Highter Contract Objects," in 1987 IEEE Ultrasonics Symposium, 903-906, (IEEE Cat. No. 87ch2492-7).

S.J. Norton, "Iterative Seismic Inversion," Gerphysical Journal, No. 94, pp. 457-468 (1988).

T.K. Sarkar, E. Arkas, and S.M. Rao (1986) "Application of FFT and the Conjugate Gradient Method for the Solution of Electromagnetic Radiation from Electrically Large and Small Conducting Bodies," IEEE Trans. Antennas Propagat., vol. AP-34, pp. 635-640, May.

R.J. Wombel and M.A. Fiddy (1988), "Inverse Scattering Within the Distorted-wave Born Approximation," Inverse Problems 4 (1988).

Y. Zhou, S.A. Johnson, M.J. Berggren, B. Carruth, and W.W. Kim, "Constrained Reconstruction of Object Acoustic Parameters from Noisy Ultrasound Scattering Data," Proc. of the IEEE 1987 Ultrasonics Symposium pp. 897-901 (1987).

Kostas T. Ladas and A. J. Devaney, "Iterative Methods in Geophysical Diffraction Tomography," Inverse Problems 8 (1992).

M.J. Berggren, S.A. Johnson, W.W. Kim, D.T. Borup, R.S. Eidens and Y. Zhou, "Acoustic Inverse Scattering Images from Simulated Higher Contrast Objects and from Laboratory Test Objects," Acoustical Imaging 16, Chicago, Illinois, Jun. 1987.

Brent S. Robinson and James F. Greenleaf, "An Experimental Study of Diffraction Tomography Under the Born Approximation," Acoustical Imaging 18, No. 18, Jun. 1990.

M.J. Berggren, S.A. Johnson, B.L. Carruth, W.W. Kim, F. Stenger and P.L. Kuhn, "Performance of Fast Inverse Scattering Solutions for the Exact Helmholtz Equation Using Multiple Frequencies and Limited Views," Acoustical Imaging 15, Halifax, Nova Scotia, Jul. 1986.

W.W. Kim, S.A. Johnson, M.J. Berggren, F. Stenger and C.H. Wilcox, "Analysis of Inverse Scattering Solutions from Single Frequency, Combined Transmission and Reflection Data for the Helmholtz and Riccati Exact Wave Equations," Acoustical Imaging 15, pp. 359-369, Plenum Press (1987).

E.J. Ayme-Bellegarda and T.M. Habashy, "Forward Ultrasonic Scattering from Multidimensional Solid or Fluids Inclusions Buried in Multilayered Elastic Structures," IEEE Trans. Ultras., Ferro., and Freq. Cont., vol. 39, No. 1, Jan. 1992.

E.J. Ayme-Bellegarda, and T.M. Habashy, "Ultrasonic Inverse Scattering of Multidimensional Objects Buried in Multilayered Elastic Background Structures," IEEE Trans. Ultras., Ferro, and Freq. Cont., vol. 39, No. 1, Jan. 1992.

J.K. Cohen and F.G. Hagin, "Velocity Inversion Using a Stratified Reference," Geophysics, 50, 11, 1985.

E. Crase, A. Pica, M. Noble, J. McDonald, and A. Tarantola, "Robust Elastic Nonlinear Waveform Inversion: Application to Real Data," Geophysics, 55, 5 (May 1990).

Peter Mora, "Nonlinear Two-dimensional Elastic Inversion of Multioffset Seismic Data," Geophysics, vol. 52, 9, Sep. 1987.

G.S. Pan, R.A Phinney and R.I. Odom, "Full-waveform Inversion of Plane-wave Seismograms in Stratified Acoustic Media: Theory and Feasibility," Geophysics, vol. 53, 1 (1988).

G.R. Franssens, "Calculation of the Elasto-dynamic Green's Function in Layered Media by Means of a Modified Propagator Matrix Method," Geophys. J.R. astr. Soc. 1983.

B.L.N. Kennett and N.J. Kerry, "Seismic Waves in a Stratified Half Space," Geophys. J.R. astr. Soc. 57, pp. 557-583, 1979.

* cited by examiner

Ultrasound System Block Diagram

Compute Node Block Diagram

Software Drivers and Interfaces Diagram

BREAST SCANNING SYSTEM

Priority is claimed to U.S. Provisional Patent Application No. 60/461,871, filed Apr. 9, 2003.

BACKGROUND OF THE INVENTION

1. Field of the Invention

The present invention relates generally to a breast scanning system.

2. Related Art

Other than skin cancer, breast cancer is the most common cancer among women, and is the second leading cause of cancer death in women, after lung cancer. According to the American Cancer Society, about 215,990 women in the United States will be found to have invasive breast cancer in 2004, and about 40,110 women will die from the disease.

Approximately 44.5 million women in the United States are screened for breast cancer each year with 10% or 4.5 million referred for a second diagnostic test. The latest American Cancer Society Breast Cancer Statistics report indicates that 1 in 7 women will get breast cancer during her lifetime. The current standard of care has significant problems, generating unacceptably high rates of false positive tests—between 8% and 10%—and upwards of 15% false negative tests. The result is that many women suffer from unnecessary and invasive biopsies. In addition, each year the U.S. healthcare system spends an estimated $2.1 billion on biopsies, which yield negative results more than 75% of the time.

Breast cancer is a malignant tumor that has developed from cells of the breast. A malignant tumor is a group of cancer cells that may invade surrounding tissues or spread (metastasize) to distant areas of the body. The female breast is made up mainly of lobules (milk-producing glands), ducts (milk passages that connect the lobules to the nipple), and stroma (fatty tissue and connective tissue surrounding the ducts and lobules, blood vessels, and lymphatic vessels). Lymphatic vessels are like veins, except that they carry lymph instead of blood. Lymph is a clear fluid that contains tissue waste products and immune system cells (cells that are important in fighting infections). Lymph nodes are small bean-shaped collections of immune system cells that are found along lymphatic vessels. Cancer cells can enter lymphatic vessels and spread to lymph nodes. Most, lymphatic vessels in the breast connect to lymph nodes under the arm (axillary lymph nodes). Some lymphatic vessels connect to lymph nodes inside the chest (internal mammary nodes) and either above or below the collarbone (supra- or infraclavicular nodes). When breast cancer cells reach the axillary (underarm) lymph nodes, they may continue to grow, often causing the lymph nodes in that area to swell. If breast cancer cells have spread to the underarm lymph nodes, they are more likely to have spread to other organs of the body as well. Thus, it is important to find out if breast cancer has spread to the axillary lymph nodes when choosing a treatment.

Most breast lumps are not cancerous, that is, they are benign. Most lumps turn out to be fibrocystic changes. The term "fibrocystic" refers to fibrosis and cysts. Fibrosis is the formation of fibrous (or scar-like) connective tissue, and cysts are fluid-filled sacs. Fibrocystic changes can cause breast swelling and pain. This often happens just before a period is about to begin. The breast may feel nodular, or lumpy, and, sometimes, a clear or slightly cloudy nipple discharge is noticed. Benign breast tumors such as fibroadenomas or papillomas are abnormal growths, but they are not cancer and cannot spread outside of the breast to other organs. They are not life threatening.

Although widespread use of screening mammography has increased the number of breast cancers found before they cause any symptoms, some breast cancers are not found by mammography, either because the test was not done or because even under ideal conditions mammography cannot find every breast cancer. The most common sign of breast cancer is a new lump or mass. A painless, hard mass that has irregular edges is more likely to be cancerous, but some rare cancers are tender, soft, and rounded. For this reason, it is important that a health care professional who is experienced in diagnosing breast diseases check any new breast mass or lump.

Other signs of breast cancer include a generalized swelling of part of a breast (even if no distinct lump is felt), skin irritation or dimpling, nipple pain or retraction (turning inward), redness or scaliness of the nipple or breast skin, or a discharge other than breast milk. Sometimes a breast cancer can spread to underarm lymph nodes even before the original tumor in the breast tissue is large enough to be felt.

If there is any reason to suspect breast cancer, other tests must be performed. After a complete physical exam (including a clinical breast exam), doctors often recommend a diagnostic mammogram or a breast ultrasound. A clinical breast examination (CBE) is an exam of the breasts by a health professional, such as a doctor, nurse practitioner, nurse, or physician assistant. The examiner first looks at the breasts for changes in size or shape. Then, using the pads of the finger tips, the breasts are felt for lumps.

Although mammograms are mostly used for screening, they can also be used to examine the breast of a woman who has a breast problem. This can be a breast mass, nipple discharge, or an abnormality that was found on a screening mammogram. In some cases, special images known as cone views with magnification are used to make a small area of altered breast tissue easier to evaluate. A diagnostic mammogram may show that a lesion (area of abnormal tissue) has a high likelihood of being benign (not cancer). In these cases, it is common to ask the woman to come back sooner than usual for a recheck, usually in 4 to 6 months. On the other hand, a diagnostic mammogram may show that the abnormality is not worrisome at all, and the woman can then return to having routine yearly mammograms. Finally, the diagnostic work-up may suggest that a biopsy is needed to tell if the lesion is cancer.

Ultrasound, also known as sonography, uses high-frequency sound waves to outline a part of the body. High-frequency sound waves are transmitted into the area of the body being studied and echoed back. A computer or dedicated electronic circuitry picks up the sound wave echoes and changes them into an image that is displayed on a computer screen. Breast ultrasound is sometimes used to evaluate breast abnormalities that are found during mammography or a physical exam. One of the most common abnormalities that women have is fibrocystic disease. Ultrasound is useful for detecting fibrocystic disease. It is the easiest way to tell if a cyst is present without placing a needle into it to draw out fluid. It can also find some breast masses. Conventional medical ultrasound uses a single ultrasound array to both transmit and receive echoes and thereby measure the ultrasound reflectivity and distance of various objects under the skin surface. It assumes that the speed of sound is constant through the tissue being imaged. It has difficulty imaging objects with low reflectivity or high absorption of sound. It produces images which are two-dimensional, distorted, grainy, and contain speckle. Foreground objects tend to mask deeper structures.

A biopsy is done when mammograms, ultrasound, or the physical examination finds a tumor. A biopsy is the only way to tell if cancer is really present. All biopsy procedures remove a tissue sample for examination under a microscope. There are several types of biopsies, such as fine needle aspiration biopsy, core (large needle) biopsy, and surgical biopsy. Each type of biopsy has distinct advantages and disadvantages. The choice of which to use will depend on the specific situation. Some of the factors the doctor will consider include how suspicious the lesion appears, how large it is, where in the breast it is located, how many lesions are present, other medical problems the patient may have, and the patient's personal preferences. Statistically, three of four biopsies are benign.

SUMMARY OF THE INVENTION

It has been recognized that it would be advantageous to develop a system and method to facilitate diagnosis of breast cancer and reduce unnecessary biopsies through improved and advanced tomography or ultrasonic scanning.

The invention provides a breast scanning system configured to scan a breast of a patient with transducer arrays that transmit and receive ultrasound signals in a bath containing a medium, such as liquid, water or gel. A table is disposable over the bath to receive the patient thereon, and has an aperture formed in the table and positionable over the bath to receive the breast of the patient pendent therethrough and into the bath.

In accordance with a more detailed aspect of the present invention, the system can include a horizontal table that is linearly vertically displaceable with respect to the bath between 1) a lowered position where the table is adjacent the bath to position the breast within the bath, and 2) a raised position where the table is spaced-above the bath to elevate the breast above the bath. In addition, the system can include means for maintaining the table in the raised position with the table spaced-above the bath.

In accordance with another more detailed aspect of the present invention, the system can include a preconditioning tank fluidly coupled to the bath to precondition the liquid prior to being introduced into the bath. In addition, the system can include means for transferring liquid from the preconditioning tank to the bath.

In accordance with another more detailed aspect of the present invention, the system can include means for securing the breast within the bath. The means for securing the breast within the bath can include a breast magnet with a breast connector to secure the breast magnet to the breast of the patient. A bath magnet can be disposed in the bath and magnetically coupleable to the breast magnet when the table is in the lowered position. In addition, a beveled cup can be associated with one of the breast or bath magnets to center the breast or bath magnets. A rod can be attached to the bath magnet and vertically movable within the bath.

In accordance with another more detailed aspect of the present invention, the system can include a plurality of table inserts each insertable into the table and each having a different sized aperture formed therein.

In accordance with another more detailed aspect of the present invention, the system can include an annular projection formed around the aperture in the table and extending beyond a lower surface of the table.

In accordance with a more detailed aspect of the present invention, the system can include a counter-bore formed in a lower surface of the table around the aperture, and sized to receive an upper portion of the bath when the table is in the lowered position.

In accordance with a more detailed aspect of the present invention, the system can include an annular channel disposed around an upper edge of the bath.

Additional features and advantages of the invention will be apparent from the detailed description which follows, taken in conjunction with the accompanying drawings, which together illustrate, by way of example, features of the invention.

DETAILED DESCRIPTION

Figure 1:
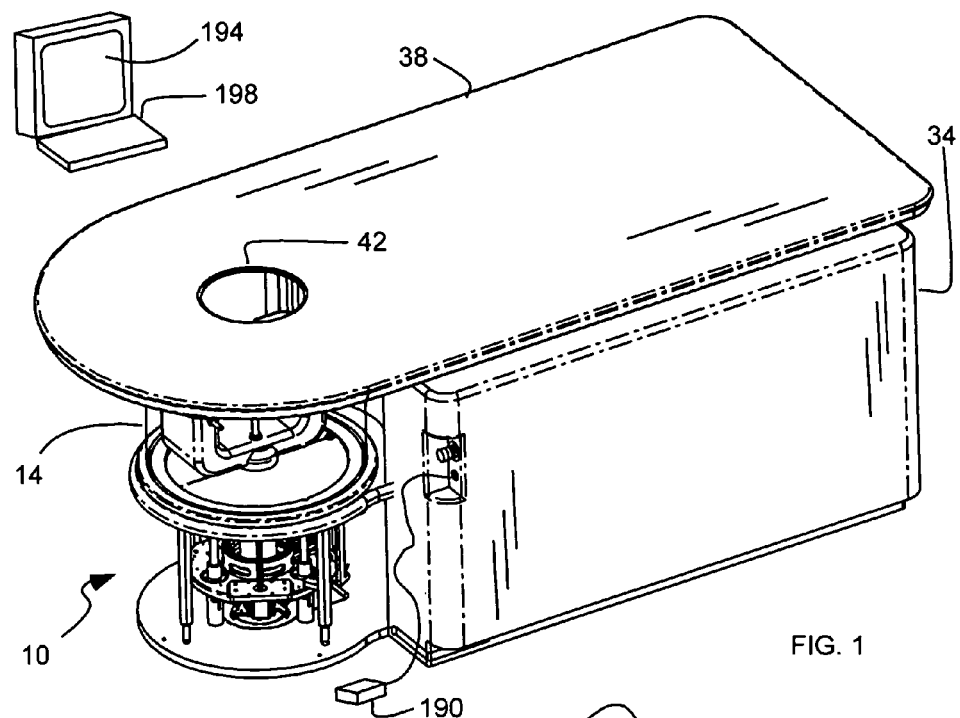
FIG. 1 is a perspective view of a breast scanning system in accordance with an embodiment of the present invention, shown with a table in a lowered position.
Figure 2:
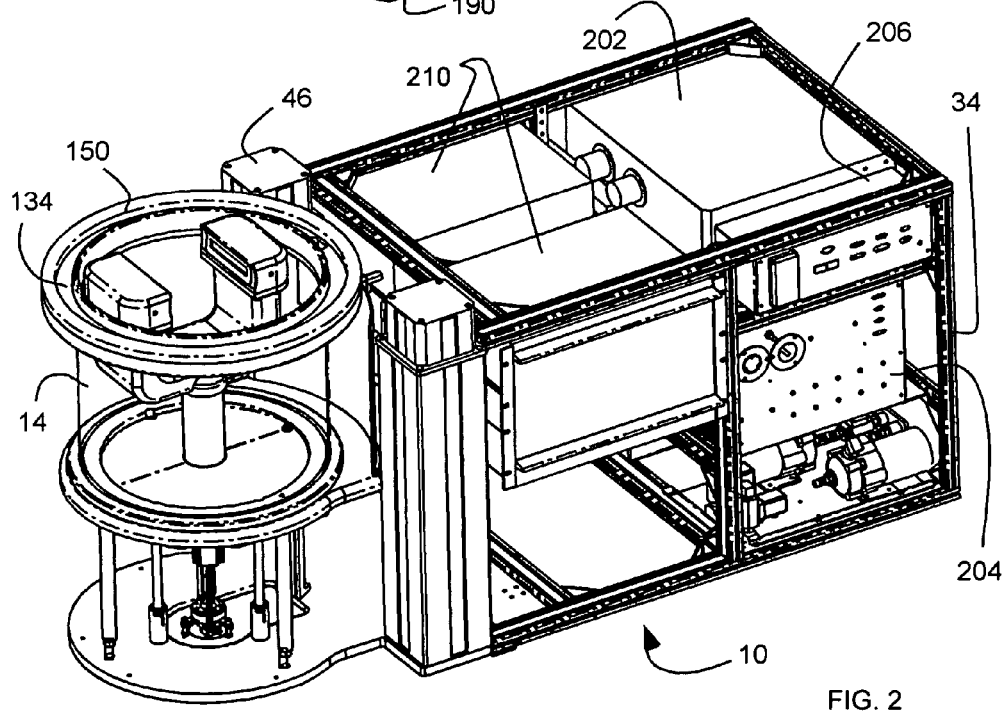
FIG. 2 is a partial perspective view of the breast scanning system of FIG. 1 with the table and outer skin or skirt removed.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in FIGS. 1-4, a breast scanning and/or imaging system, indicated generally at 10, in accordance with the present invention is shown for use in the diagnosis of breast cancer. The system can be a non-invasive, diagnostic tool to provide detailed information about the physiology (i.e. bulk tissue properties) and anatomy (i.e. physical architecture) of the breast. The system can be used as an adjunct to mammography to aid physicians in diagnosing breast cancer by providing information about tissue properties that help to more clearly differentiate normal or benign form malignant tissue in the breast. The system can replace other diagnostic testing, such as diagnostic mammograms, breast ultrasound, and other imaging technologies currently used between a screening mammogram and a biopsy.

In general, the system 10 can use ultrasound inverse scattering technology to produce a 3-D stack of tomography (2-D planar slice) images (similar in appearance and spatial resolution to CT or MR imaging methods). Direct 3-D imaging is a further feature of the system 10. These images can be produced using two different techniques, namely Ultrasound Reflective Tomography (URT) and Ultrasound Inverse Scattering Tomography (UIST). Compared with conventional projection mammography, URT images can be more detailed, easier to read, and do not use potentially harmful ionizing radiation. Unlike conventional ultrasound, ultrasound images using inverse scattering technology completely penetrate and sample the entire breast for uniformity and better overall resolution. In addition, such images are quantitative representations of ultrasound tissue properties, and therefore are not dependent on the system operator for image quality and consistency. The images can be reconstructed in three dimensions providing an important visualization tool for diagnosis, biopsy and surgery staging.

The system 10 can use two ultrasound arrays that rotate around the breast, generating true 3-D images and diagnostic information in a commercially viable timeframe, such as less than 20 minutes per exam. The breast (shown in phantom lines in FIG. 8) can be disposed in a bath 14 of medium, such as liquid, water or gel. The use of water will be described throughout for illustrative purposes. The system 10 can include two opposing ultrasound transducer arrays 18 and 20 (FIGS. 7a and 8) movably disposed in the bath 14 to obtain both reflection and transmission information used to generate images and diagnostic information. The arrays 18 and 20 are mechanically designed to rotate and move up and down generating a complete 3-D data set for the area of interest or even for the entire breast. Ultrasound pulses can be used for two imaging modalities: reflective and transmissive. For reflective images, the system emits a pulse from one array and receives the reflected energy back in the same array. The array can emit a pulse at 20 positions (every 18 degrees) around the breast. During the same rotation sequence, the transmitting array can emit an ultrasound signal into and through the breast at 180 different locations (every 2 degrees) around the entire breast. The resulting waveforms are received by the opposing array. This allows the system to simultaneously generate data for both reflection and transmission sound properties of the breast. Alternatively, the arrays can move and/or emit continuously.

The imaging system produces three separate images using two different imaging techniques: 1) transmission information generates images representing bulk tissue properties of speed of sound and attenuation of sound at each point in the breast; and 2) data generated from reflection information generates detailed reflective tomographic images that are refraction corrected. These imaging techniques are combined to effectively produce a three-dimensional stack of "slices" of the breast. Data from the ultrasound source is analyzed, and a quantitative map of tissue properties is rendered. In the "transmission mode" the energy propagates through the breast (or other soft tissue). In the "reflection mode", the energy reflects back to the receivers. In both cases, the energy of the acoustic wave is refracted and scattered from the tissue it encounters. In this process multiple physical phenomena take place: reflection, refraction, diffraction, and multiple scattering events. These effects are generally ignored in present ultrasound, which seriously degrades the image, therefore rendering it useful only in differentiating architectural or structural properties within the breast. In present ultrasound it is impossible to acquire quantitative values at a level sufficient for diagnosis of tissue characteristics using standard reflection ultrasound or imaging.

Further details of inverse scattering technology and imaging are disclosed in U.S. Pat. Nos. 4,662,222; 5,339,282; 6,005,916; 5,588,032; 6,587,540 and 6,636,584, which are herein incorporated by reference in their entirety.

Figure 7A:
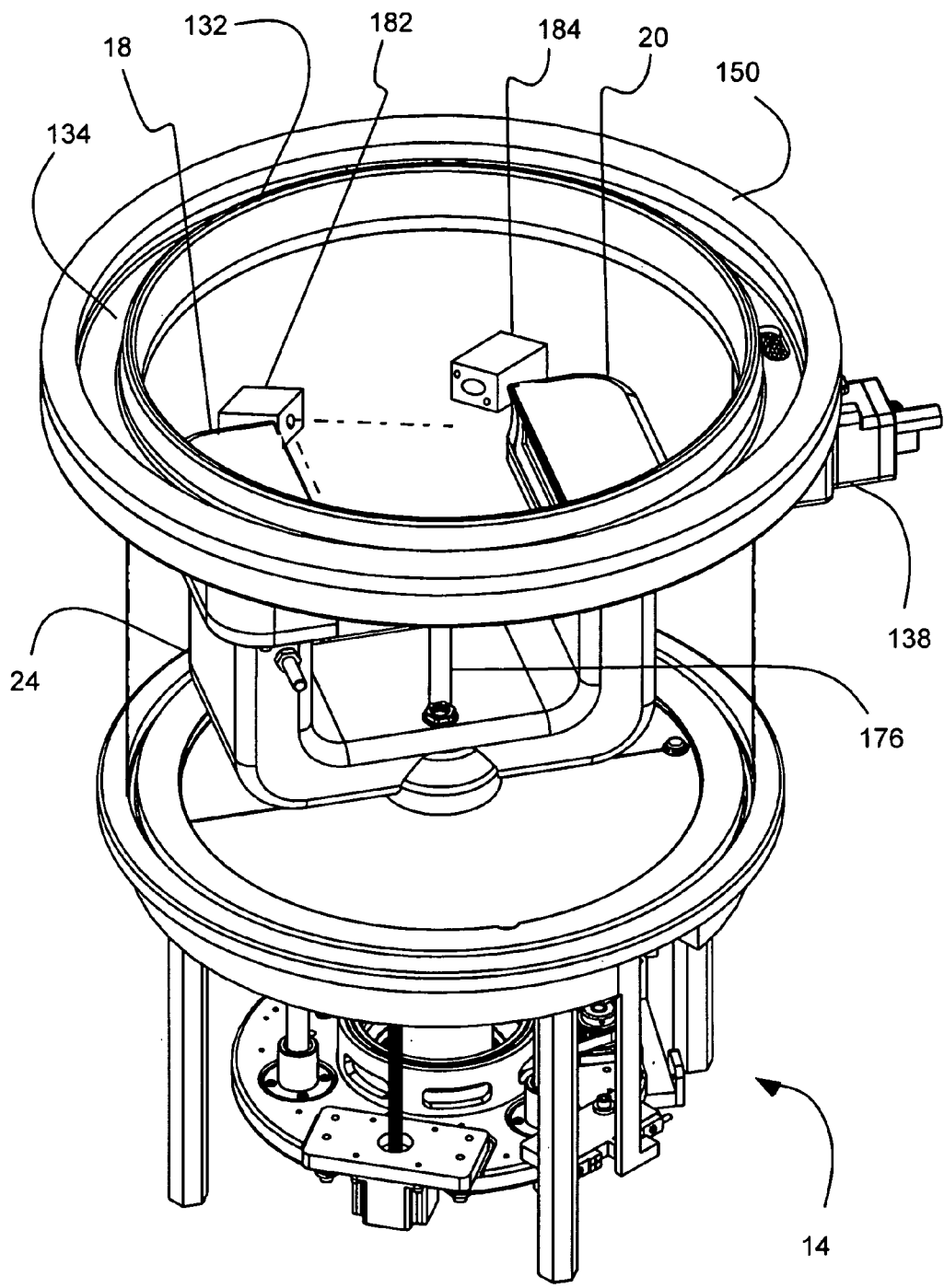
FIG. 7a is a perspective view of a bath of the breast scanning system of FIG. 1.
Figure 8:
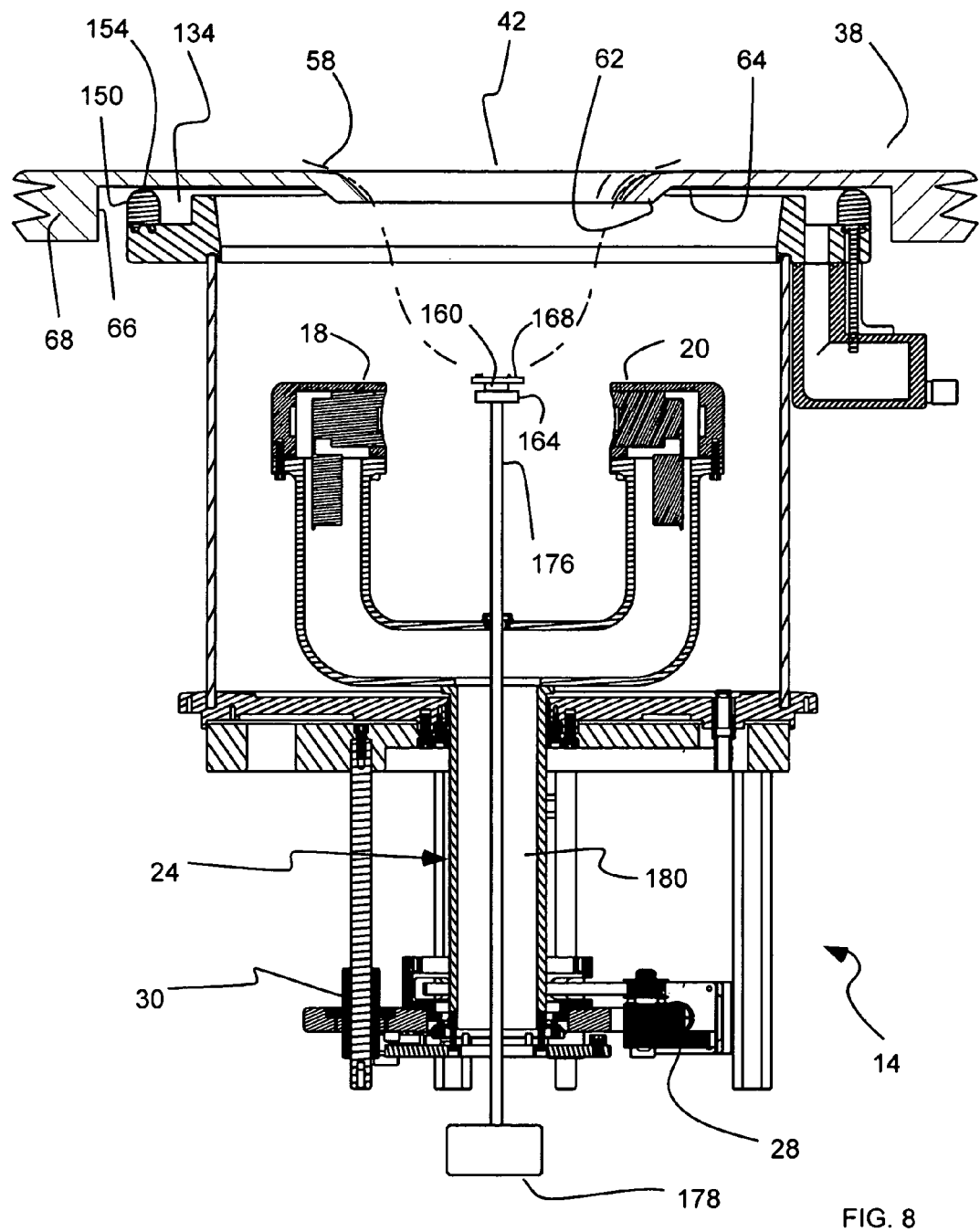
FIG. 8 is a cross-sectional side view of the bath of FIG. 5.

Referring to FIGS. 7a and 8, the transducer arrays 18 and 20 can be disposed in the bath 14, and carried by an armature 24, also disposable in the bath 14. The armature 24 can include a u-shaped member disposed on a vertical column that extends through a bottom of the bath. Each vertical arm of the u-shaped member can carry one of the arrays. The u-shaped member can be sized to position the arrays around the breast. The arrays 18 and 20 can be rotatable around an axis of rotation, and displaceable vertically. For example, the armature can rotate around the vertical column, thus rotating the arrays. A rotational motor 28 can be coupled to the armature 24 to rotate the armature. For example, the rotational motor can be a rotational step motor coupled to the armature or vertical column by a belt. In addition, a linear motor 30 can be coupled to the armature 24 to linearly displace the armature, and thus the transducer arrays. For example, the vertical column can be carried by a platform on a plurality of rods. One of the rods can be threaded. The linear motor can engage the threaded rod such that rotation of the motor can raise and lower the platform, and thus the vertical column along with the rotational motor 28. A rotational and/or sliding seal can be formed between the bath 14 and the armature 24, or vertical column, to seal the bath where the armature or vertical column passes through the bottom of the bath. In addition, one or more bearings or rotational bearings can be disposed between the vertical column and the platform to facilitate rotation and reduce frictional forces. Thus, the platform can carry the armature and related motors to move the armature.

Figure 7B:
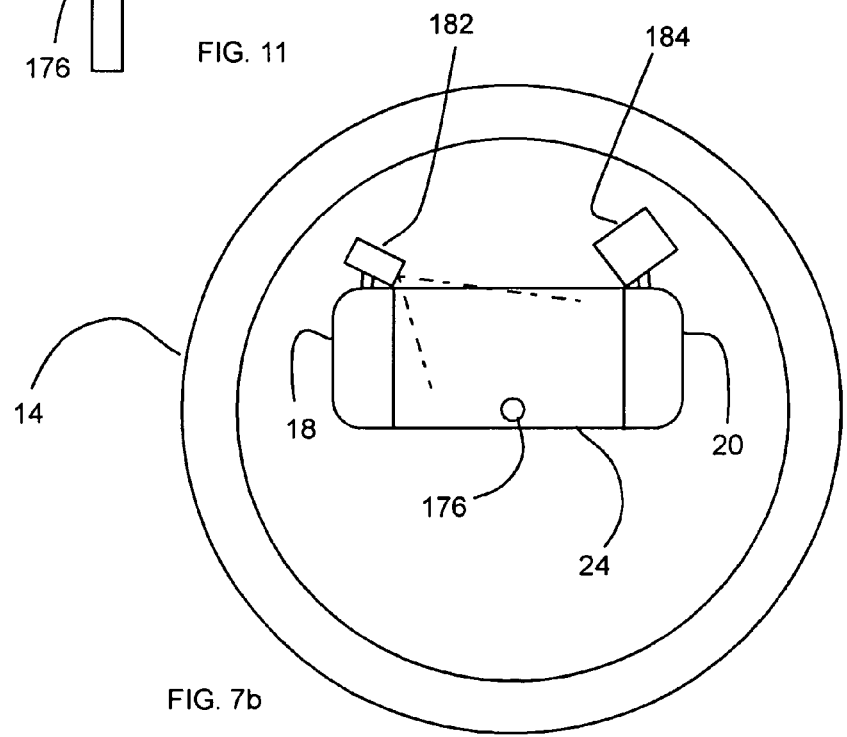
FIG. 7b is a top view of the bath of the breast scanning system of FIG. 1.

The transducer arrays 18 and 20 can be off-set, or non-concentric, with respect to an axis of rotation, as shown in FIG. 7b. The armature 24 can also be offset or non-concentric with respect to the axis of rotation.

The transducer arrays 18 and 20 can send and receive ultrasound signals at a plurality of elevational locations along the breast, and at a plurality of rotational orientations around the breast at each elevational location. The linear motor 30 can move (raise or lower) the transducer arrays sequentially through a plurality of different elevational locations along the breast. The rotational motor 28 can sequentially move (or rotate) the transducer arrays through a plurality of different angular orientations around the breast at each elevational location. As described above, arrays can emit a pulse at 20 positions (every 18 degrees) around the breast. During the same rotation sequence, the transmitting array can emit an ultrasound signal into and through the breast at 180 different locations (every 2 degrees) around the entire breast. The resulting waveforms are received by the opposing array. The arrays can then be moved to a different location along the breast and the sequence repeated. Alternatively, the arrays can emit during a continuous motion. Thus, the movement of the arrays and armature can be discrete, or stepwise through discrete position, or continuous.

In addition, the arrays 18 and 20 can be tilted, or rotatable to have tilted orientation to allow imaging closer to the chest wall. For example, the arrays can be angled or directed in an upwardly angled direction so that the arrays emit upwardly at an angle and receive downwardly at an angle.

Alternatively, transducers can be configured or arrayed differently to have different movement, or even no movement. For example, transducers can be vertically oriented along the length of the breast, and can be rotated around the breast, without the need to move the transducers vertically. Alternatively, transducers can be horizontally oriented around the circumference of the breast, and can be moved vertically along the length of the breast, without the need to rotate the transducers. Furthermore, the transducers can be disposed around the breast, and along the length of the breast, so that the transducers do not have to be moved or rotated.

The bath 14 can be cylindrical and transparent, or can have a bath wall that is cylindrical and transparent. The bath can be any desired shape, but cylindrical is believed to be the most efficient because it matches or allows the rotational motion of the arrays while minimizing volume. The transparent wall allows the breast to be viewed during the scan, and allows a technician to observe operation of the armature. Alternatively, the bath wall can be opaque or translucent, and can have a window formed therein. The bath can include one or more holes therein forming inlet and/or outlet openings to allow fluid to enter and/or exit the bath. An upper end of the bath can be open to receive the breast, as described in greater detail below.

Referring to FIGS. 1-4, the bath 14 can be supported by or disposed on a base 34. The base can include a framework and can contain various components of the system, as described in greater detail below. A skin or skirt can be disposed around the base, or portions thereof, to protect and restrict access to the various components. The bath 14 can be disposed at one end of the system or base 34 to increase the viewing angle or viewing perimeter. The base can include controls, such as an emergency shut-off or stop button. In addition, the base can include various input/output connections, such as for controls.

A horizontal table 38 can be disposable over the bath 14 and the base 34 to receive the patient thereon. The table 38 can be rigid, but can have a padded upper surface for patient comfort. The table 38 can be supported or carried by the base 34. An aperture 42 can be formed in the table 38 and positionable over the bath 14. In use, the patient's breast is received pendent through the aperture (as shown in phantom lines in FIG. 8), and into the bath. The aperture 42 can be located nearer one end of the table. The end of the table with the aperture can be broadly curved to circumscribe the bath and/or the aperture. The curved end of the table facilitates access to the bath and/or breast, and facilitates viewing the bath and/or breast.

Figure 3:
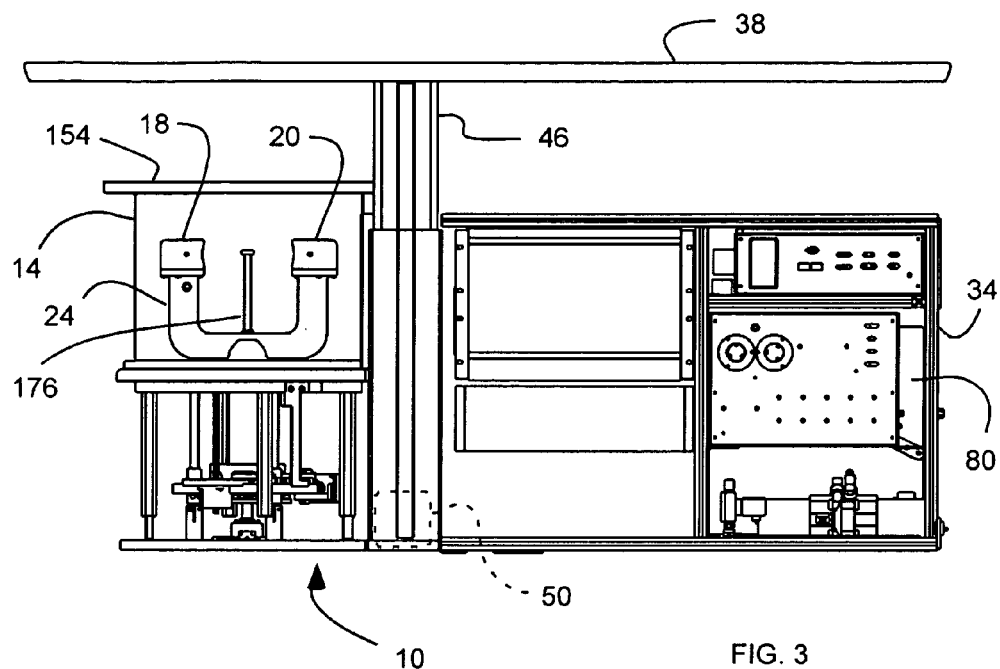
FIG. 3 is a partial side view of the breast scanning system of FIG. 1, shown with the table in a raised position and the outer skin or skirt removed.
Figure 4:
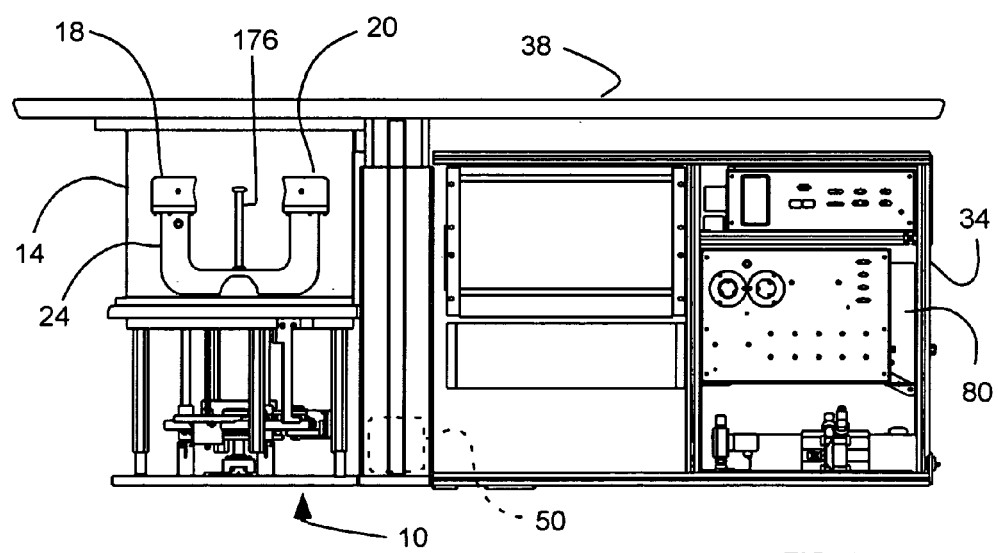
FIG. 4 is a partial side view of the breast scanning system of FIG. 1, shown with the table in the lowered position and the outer skin or skirt removed.

The table 38 and the bath 14 can be linearly vertically displaceable with respect to one another. For example, the table 38 can be movable upward and downward, away from and towards the bath. The table 38 can have a lowered position, as shown in FIGS. 1, 4 and 8, and a raised position, as shown in FIG. 3. In the lowered position (FIGS. 1, 4 and 8), the table 38 is adjacent the bath to position the breast within the bath. In the raised position (FIG. 3), the table 38 is spaced-above the bath to elevate the breast above the bath. The raised position allows access to the breast by a technician or physician. For example, a technician can center the breast in the aperture 42, and/or draw the breast further through the aperture.

One or more columns 46 can support the table 38. For example, a pair of columns 46 can be disposed on each side of the base 34. One or more motors 50 can be coupled to the columns 46 to raise and lower the columns, and thus the table. The motors can be located within the columns, and can be rotational motors providing relative rotational movement between a threaded screw and a threaded nut to provide linear motion. The column(s) and motor are one example of means for maintaining the table in the raised position with the table spaced-above the bath, and means for raising and lowering the table.

Figure 5:
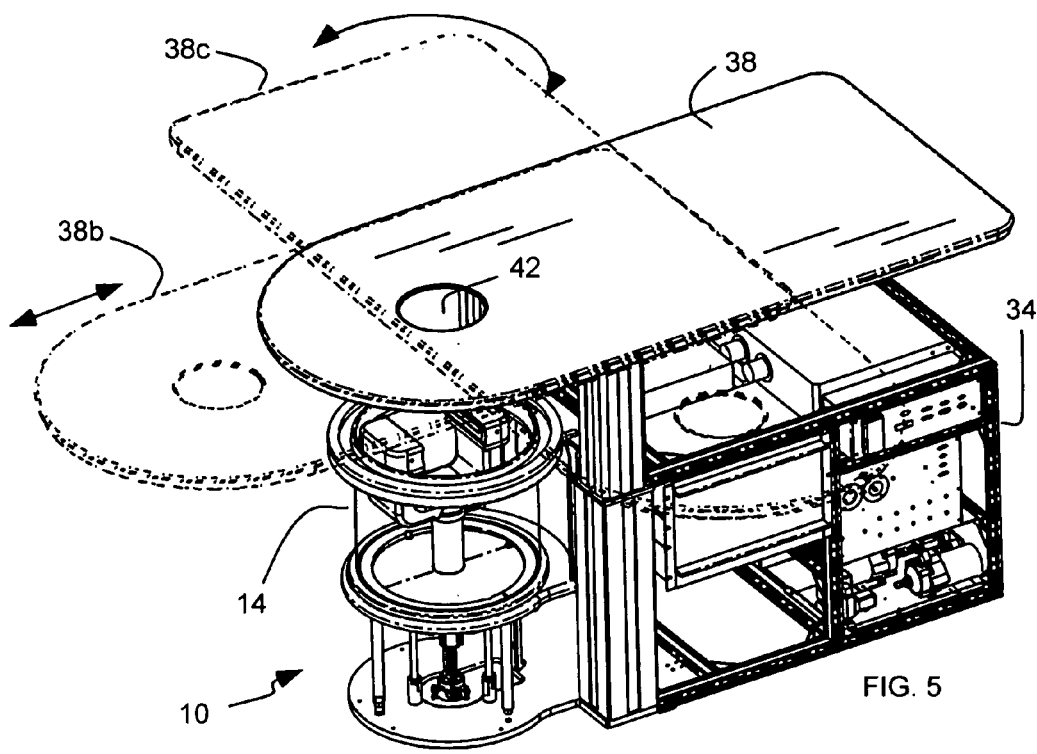
FIG. 5 is a perspective view of the breast scanning system of FIG. 1, shown with the table in the raised position, shown with the outer skin or skirt removed.
Figure 6:
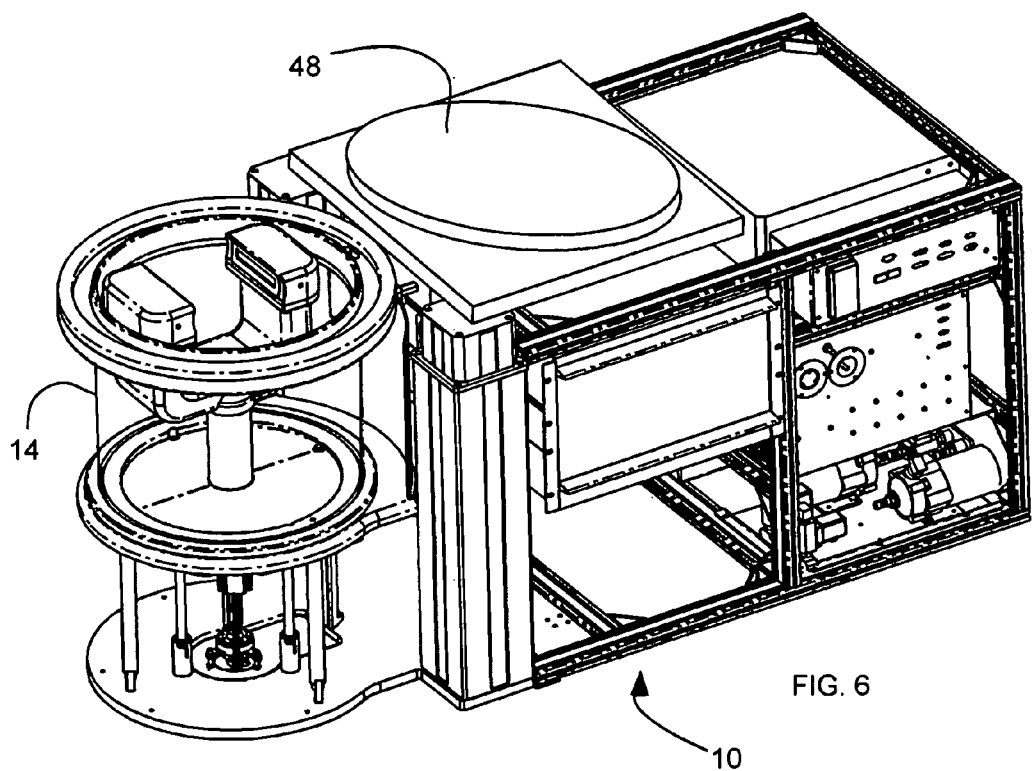
FIG. 6 is a partial perspective view of the breast scanning system of FIG. 1, shown with the table and outer skin or skirt removed.

Referring to FIGS. 5 and 6, the table 38 can also be displaceable horizontally, as shown in dashed lines, so that the aperture 42 can be displaced away from the bath 14 to allow further access to the breast for additional procedures, such as biopsies. For example, the table 38 can be linearly displaceable, such as longitudinally in a forward direction, indicated by 38b. A linear slider can be disposed between the columns and the table to allow the table to slide. As another example, the table 38 can be rotationally or pivotally disposed on the base, indicated by 38c. A rotational bearing 48 can be disposed between the columns and table to allow the table to pivot or rotate, as shown in FIG. 6.

Figure 10:
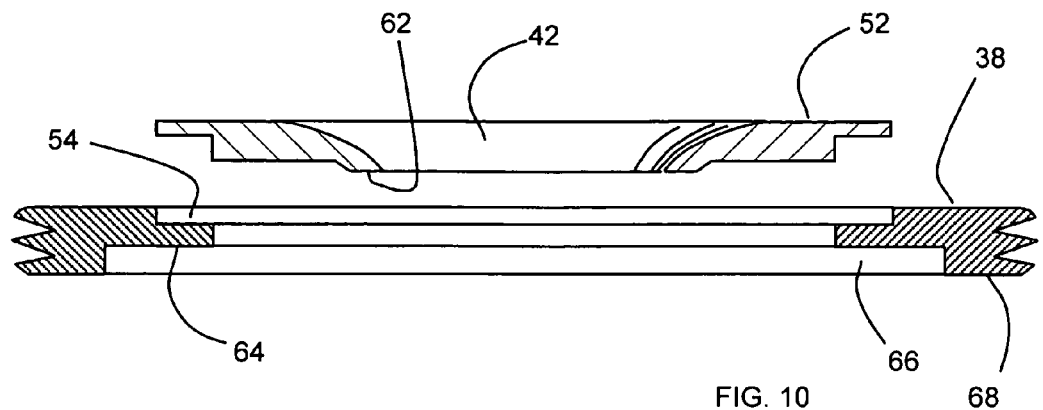
FIG. 10 is a partial cross-sectional view of the table of FIG. 1.

The aperture 42 in the table 38 can be sized to match the patient's breast. Referring to FIG. 10, a table insert 52, with the aperture 42 therein, can be insertable into the table 38. The table 38 can have a cavity with a flange 54 to support the table insert 52. The table insert can be flush with the table, or upper surface thereof. The system or table can be provided with a plurality of table inserts, each with a different sized aperture, to match the size of the patient's breast. Sizing the aperture 42 to the patient's breast can result in greater comfort to the patient, and can allow a maximum amount of the breast to extend through the aperture.

Referring to FIG. 8, the aperture 42 can have a rounded or curved edge 58, or an edge with a radius. The curved edge 58 can provide patient comfort. In addition, the curved edge 58 can reduce the thickness of the table proximate the aperture to allow a greater portion of the breast to extend into the bath, and thus more of the breast can be reachable by the arrays. The edge can also be beveled or chamfered.

An annular projection 62 can be formed around the aperture 42, or around a lower edge of the aperture, and can extend downward beyond a lower surface 64 of the table, or below the upper edge of the bath 14. The annular projection 62 can facilitate positioning the breast within the bath, and disposing the breast within reach of the arrays. A counter-bore 66 can be formed in a lower surface 68 of the table around the aperture 42 to receive an upper portion or upper edge of the bath 14 when the table is in the lowered position. The counter-bore 66 can be sized and shaped to match the bath. The counter-bore allows the breast to be positioned within reach of the arrays, while maintaining the strength of the table.

As discussed above, the bath 14 contains a medium, such as liquid or water. The liquid or water can have characteristics, such as purity and the like; to facilitate transmission of the signals from the arrays, or to resist interference with such transmission. For example, the liquid or water can be purified, filtered, de-ionized, degassed, etc. In addition, the liquid or water can have known qualities, such as temperature, to facilitate data calculations or conversions, and to provide patient comfort. For example, the liquid or water can have a temperature similar to normal body temperature (or approximately 30° C.).

Figure 9A:
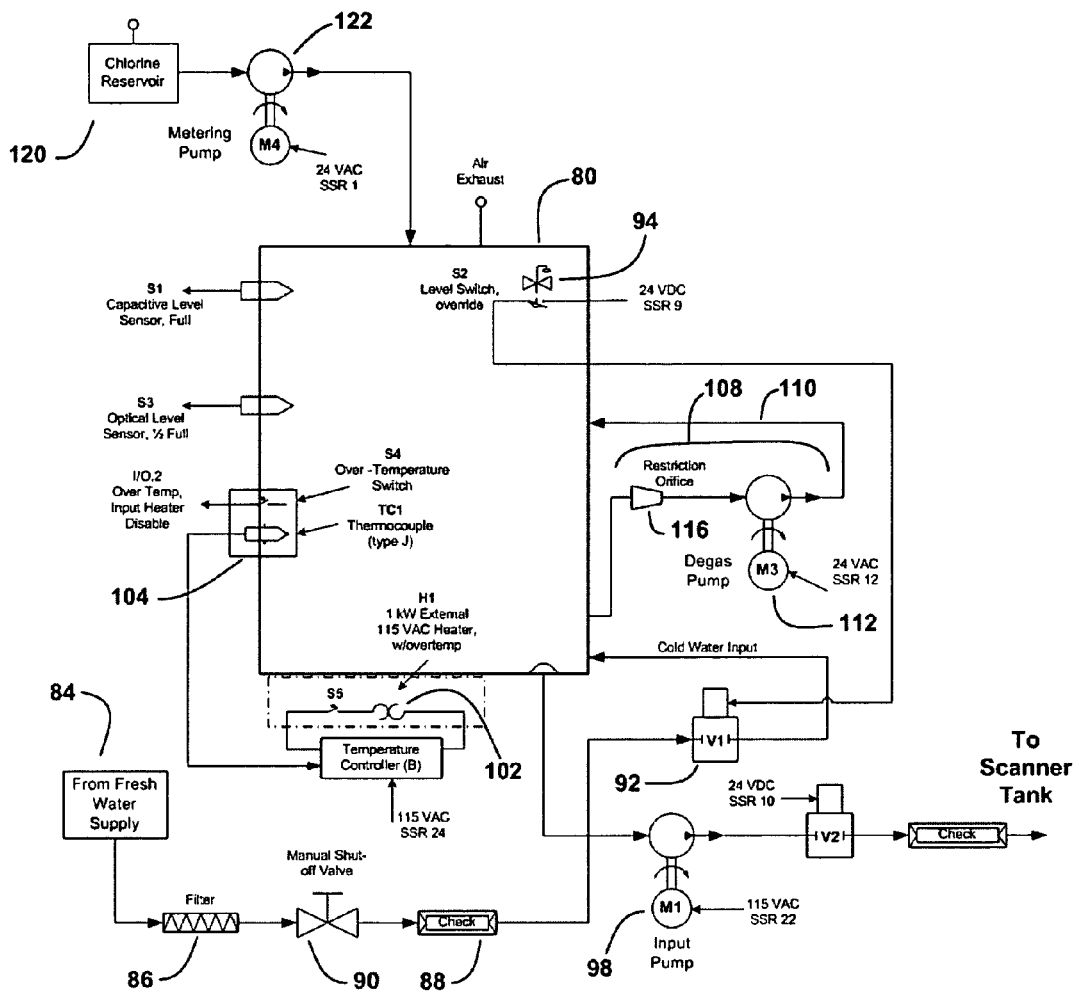
FIGS. 9a and b are schematic block diagrams of a liquid system of the breast scanning system of FIG. 1.
Figure 9B:
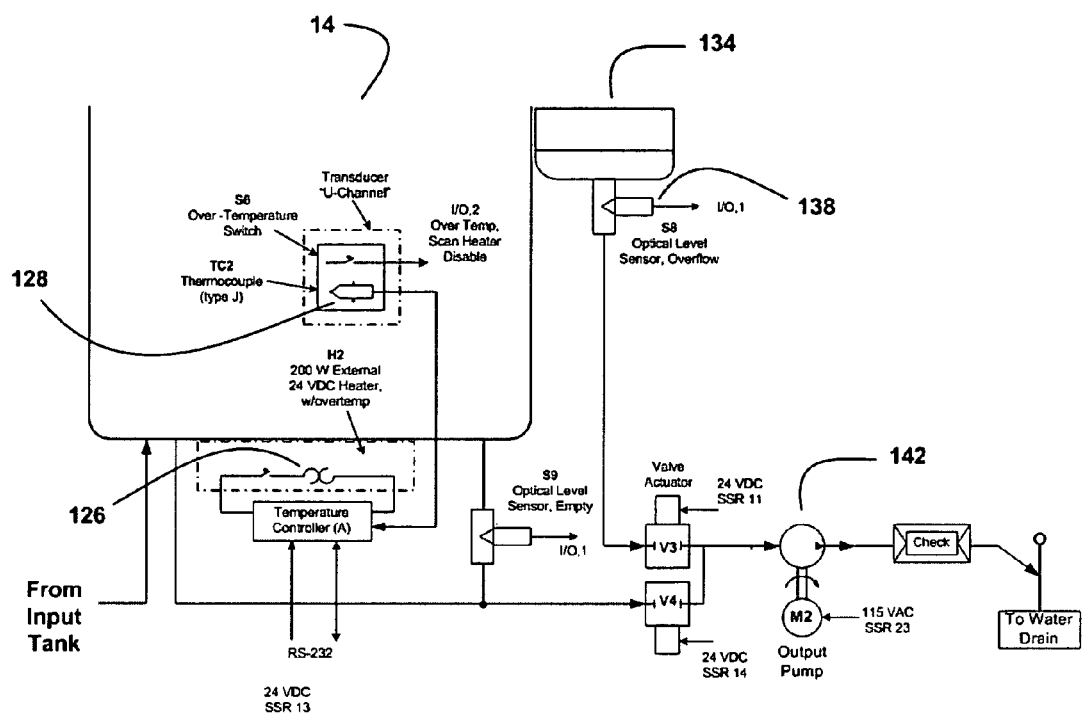

Referring to FIGS. 3, 9a and 9b, the system 10 can include a preconditioning tank 80 operatively and fluidly coupled to the bath 14 to precondition and pre-treat the liquid prior to being introduced into the bath. The preconditioning tank 80 advantageously allows the liquid to be prepared prior to use, and while the bath 14 is being used. For example, it may be necessary or desirable to flush the bath between one or more uses, or between one or more patients. Thus, while the bath is in use, the preconditioning tank can prepare another batch of liquid. It will be appreciated that the bath can have a volume or capacity of approximately 15 gallons, and that heating such a volume can take time, and can reduce patient scanning efficiency. Thus, the preconditioning tank increases efficiency, or the number of scans that can be performed or the number of patients scanned.

The preconditioning tank 80 can be disposed in the base 34 below the table for efficient use of space. The tank 80 can be coupled to a water source 84, such as a common tap or culinary water system, by a supply line, such as a hose, tubing or pipe. The water source can provide water at ambient temperature, or heated, such as from a water heater. A filter 86, check valve 88, and manual valve 90 can be coupled in the supply line. The filter 86 can act as a deionizer. An automatic or electronic valve 92 can be coupled in the supply line and coupled to a level sensor or switch 94 associated with the tank. The level sensor 94 can be any type, and can be mechanically or electrically coupled to, the valve 92 to shut off the valve when the tank is full. The tank 80 can be operatively of fluidly coupled to the bath 14 by an input line, such as a tube. An input pump 98 can be coupled to the input line to pump water from the tank 80 to the bath 14. The pump 98 and input line are examples of means for transferring liquid from the preconditioning tank to the bath. A check valve and electrical valve can also be coupled to the input line to control the flow of water into the bath.

A heater 102 can be coupled to the preconditioning tank 80 to heat the water in the tank. The heater can be an electrical resistance heater, and can be external to, and underneath, the tank. A thermocouple 104 also can be associated with the preconditioning tank 80 and operatively coupled to the heater 102.

A de-gaser 108 can be coupled to the preconditioning tank 80 to remove gas from the water. The de-gaser 108 can include a circulation circuit 110 with a recirculation pump 112 to pump water from the tank, through the circuit, and back into the tank. One or more orifices 116 can be disposed in the circulation circuit 110. The orifices 116 can be formed in a plate extending across the tubing or pipes of the circuit. The orifices have a diameter or size less than a diameter of the circulation circuit. The pump can introduce a pressure differential across the orifices that create a partial vacuum causing the gas in the water for form as bubbles and rise to the surface of the tank. An exhaust air opening can be formed in the top of the tank.

The preconditioning tank 80 can also include a reservoir 120 fluidly coupled to the preconditioning tank 80. The reservoir 120 can contain an antibacterial and/or antiviral agent, such as chlorine. A metering pump 122 can be coupled between the reservoir and the preconditioning tank to meter a predetermined amount of the agent or chlorine. The preconditioning tank can also include other systems to treat the water, such as an ozonator, filters to reduce minerals or particulates, etc.

Once treated, the water can be transferred or pumped from the tank to the bath. The bath 14 can also include a heater 126 coupled to or associated with the bath to maintain a desired temperature of the liquid or water within the bath. A thermocouple 128 can be associated with the bath and operatively coupled to the heater.

The bath 14 or upper edge 132 thereof can include an annular channel 134 or spillway that can surround or circumscribe the bath. The bath 14 can be filled until the water overflows the bath into the channel 134 or spillway. A liquid sensor 138 can be disposed in the channel to sense an overflow condition, and operatively coupled to the input pump 98. Filling the bath until it overflows insures that the water is at its highest level with respect to the breast, allowing for maximum scanning of the breast. A drain or outlet pump 142 and outlet valves can be coupled to the bath 14 to evacuate the water from the bath.

Referring to FIG. 8, a seal 150 can be disposed between the bath 14 and the table 38, such as being disposed on the upper edge 132 of the bath. The seal 150 can be compressible between the bath and the table in the lowered position. The seal 150 resists water from leaking or splashing outside of the bath and/or channel. A sensor can be disposed between the table and the bath to sense interference and stop lowering of the table. The sensor can be a pinch sensor 154 to sense pressure. The pinch sensor can be associated with the seal 150 and/or upper edge 132 of the bath.

Figure 11:
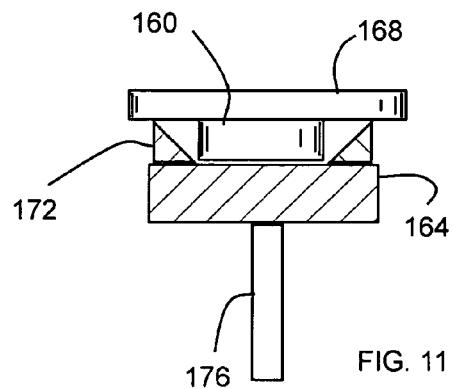
FIG. 11 is a partial cross-sectional view of a breast retention assembly of the breast scanning system of FIG. 1.

Referring to FIGS. 8 and 11, in accordance with one aspect of the invention, a breast retention assembly can be used to secure the breast within the bath. For example, a pair of magnets, including a breast magnet 160 attached to the breast and a bath magnet 164 disposed in the bath, can be used to hold the breast. The breast magnet 160 can have a breast connector 168 to secure the breast magnet to the breast of the patient. The breast connector can use an adhesive similar to that used to secure other medical sensors to the skin. The bath magnet and the breast magnet magnetically couple when the table is in the lowered position. A beveled cup 172 can be associated with one of the breast or bath magnets, such as the bath magnet, to center the breast and bath magnets with respect to one another, as shown in FIG. 11. The beveled cup can be plastic and can mechanically center the magnets. The bath magnet 164 can be movable within the bath, and can be vertically moved between a raised and a lowered position. The raised position of the bath magnet can correspond to the raised position of the table, and can allow a technician to secure the bath and breast magnets prior to lowering the table and immersing the breast in the bath. The bath magnet 164 can be disposed on and carried by a rod 176 vertically movable within the bath. The rod 176 can extend through a hollow interior 180 of the armature 24, or vertical column thereof. A seal can be formed around the rod.

The rod 176 can be raised and lowered by a motor, such as a stepper motor 178. The stepper motor can be rotational and can cause relative rotation between a threaded rod and nut to raise and lower the rod 176. The stepper motor 178 can indicate the position of the rod to control electronics, and thus the tip or nipple of the breast. Similarly, the position of the table can be determined using the motors 50. Thus, the length and position of the breast can be determined. Alternatively, sensors can be used.

The magnets and/or rod are one example of means for securing the breast within the bath. Other means for securing the breast within the bath can include, for example, attaching a shaft, wire, spring, weight, magnet, or the like at or near the nipple. As another example, means for securing the breast within the bath can include a retention device mounted to the table permitting the ultrasound tank to be lowered out of the way (or the patient raised) with the breast remaining in a known position for stereotaxic guided biopsy or other medical procedures. The retention device can include a brace rotatably mounted to the table. The brace can include a ring circumscribing the hole and rotatably coupled to the table by a bearing. A pair of posts can extend downwardly from the ring to a beam extending between the posts. A magnetic coupling can include a base magnet pivotally coupled to the beam or brace by bearings, and a nipple or breast magnet coupled to the patient's breast or nipple, and magnetically coupled to the base magnet. The bearings allow the brace, or posts and beam to rotate about the breast, thus rotating out of interference with the arrays during operation, and without twisting the patient's breast. The brace can be pivoted when abutted by the arrays. Alternatively, magnets can be disposed between the brace and arrays to resist interference between the two.

As another example, means for securing the breast within the bath can include a special bra or other membrane could be could be worn over the breast to help hold the breast in position. The bra could include a device for attaching a shaft, wire, spring, weight or magnet as described above. A membrane can be provided in the shape of a cone to receive the breast therein. The membranes can include a proximal, larger opening to receive the breast, and a distal smaller opening through which suction can be applied to draw the breast into and against the membrane. An ultrasound gel can be disposed between the breast and the membrane for lubrication and coupling.

Referring to FIGS. 7a and 7b, a light source, such as a laser pointer 182, can project a light beam (such as a fan beam) onto the breast at an area of interest. The area of interest can be marked prior to immersing the breast into the bath. The area of interest can be determined beforehand by reference to breast examinations, mammograms, etc. The laser pointer 82 can be mounted to the armature 24, and be positioned at the arrays. Thus, the armature and arrays can be raised or lowered until the light beam from the laser pointer aligns with the mark on the breast corresponding to the area of interest. This position can be saved in the system as a center of the area of interest, and the scan can begin and end at a predetermined distance above and below the center of interest. It will be appreciated that the position of the armature, and thus the arrays, can be determined from the motors used to position the armature, or from other sensors.

In addition, a camera 184 can be positioned to provide an image of the breasts and arrays. The camera can be coupled to the system and/or a display or control module associated with the system. The camera 184 can be mounted on the armature and positioned at the arrays. A horizontal line, or cross-hair, can be provided on the display, camera, or system to align the camera, and thus the arrays, with the mark on the breast corresponding to the area of interest. The camera can also include a light source, such as one or more LEDs.

Referring to FIGS. 12a-d, an architecture or hardware/software platform of the system 10 is shown. The architecture or platform can include custom boards to provide data rates fast enough to store and process the amount of data gathered by the arrays.

The architecture of hardware/software platform can look to the outside world as a Linux cluster super-computer. The cluster can include five or more nodes 250 interconnected by a high-speed Ethernet network 250. In addition, each node can have access to a global file system. Two or more of the nodes can be configured as compute nodes 258. Each computer node can include a SBC (Single Board Computer) 262 and a Fibre Channel Host Adapter 266. Two of the nodes can be configured as Data Acquisition nodes 270. Each Data Acquisition node can include a SBC 274, Fibre Channel Host Adapter 278, Waveform Generator Card 282, Data Acquisition Cards 286 and Mux Cards 290.

A Compute Node 258 can include a SBC 262, FCHA 266 and CompactPCI backplane 294 that the two cards plug into. One or more of the backplanes are installed in a 19 inch rackmount chassis. The chassis provides power and cooling to the cards plugged into the backplanes.

Each SBC 262, 274 can include a Pentium processor, 1 GB of SDRAM, an interface to the CompactPCI backplane, an onboard PCI bus that supports the following peripherals: a mouse, a keyboard, a parallel port, EIDE, USB, 10/100/1000 ethernet and a video controller.

The Fibre Channel Host Adapter card 266,278 can connect the SBC to the global file system.

The Data Acquisition Node 270 can include the SBC 274, FCHA 278, Data Acquisition (DA) Cards 286, Mux cards 290, Waveform Generator (WFG) Card 282, the CompactPCI backplane 298 that the cards plug into and a 19-inch rack mount chassis. The chassis provides power and cooling to the backplane and also provides a high-voltage power source for the Mux cards. One of the Data Acquisition Nodes is designated as a master. The Master Data Acquisition Node has a motion control card 302 in addition to the cards found in the Data Acquisition Node.

The Mux card 290 is the interface between the transducer array 18, 20 and the DA Card 286. A high density coax cable assembly connects the Mux card to the transducer array. The Mux card accepts 256 analog inputs/outputs to/from the transducer array. Through inputs for the DA Card, the Mux card selects 16 of the 256 channels for amplification (70 db) and filtering. The 16 channels of conditioned analog data are then presented to the DA card via the CPCI backplane.

The Data Acquisition Card 286 accepts analog data from the Mux Card 290. The Mux Card presents 16 channels of analog data to the DA Card. The DA card has 16 14-bit A/D chips. Each A/D chip digitizes the analog data at a rate of 33 million samples per second. Each A/D chip stores the converted data in a double-buffered fifo for later storage in the SBC's memory or directly to the Fibre Channel Host Adapter.

The Waveform Generator Card 282 is used to generate an arbitrary waveform for use by the Mux Card. The Waveform Generator card is the source of the signal used to excite the ultrasound transducer array. In addition the WFG card creates a time variable gain control also used by the Mux card to vary the gain of that card's amplifiers. The WFG also generates the master timing signals used to synchronize the entire data acquisition subsystem.

Figure 12A:
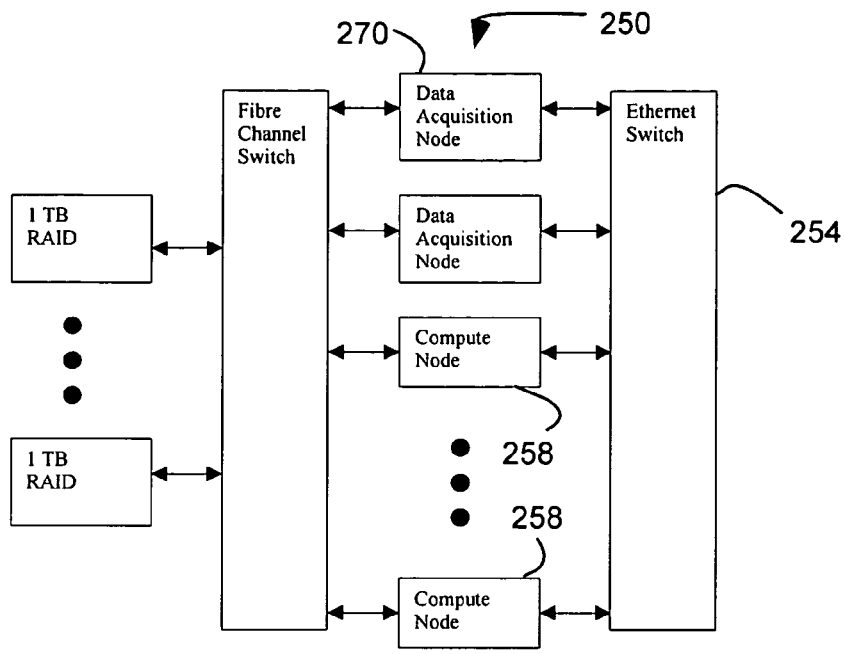
FIGS. 12a-d are block diagrams of the architecture or hardware/software platform of the breast scanning system of FIG. 1.
Figure 12B:
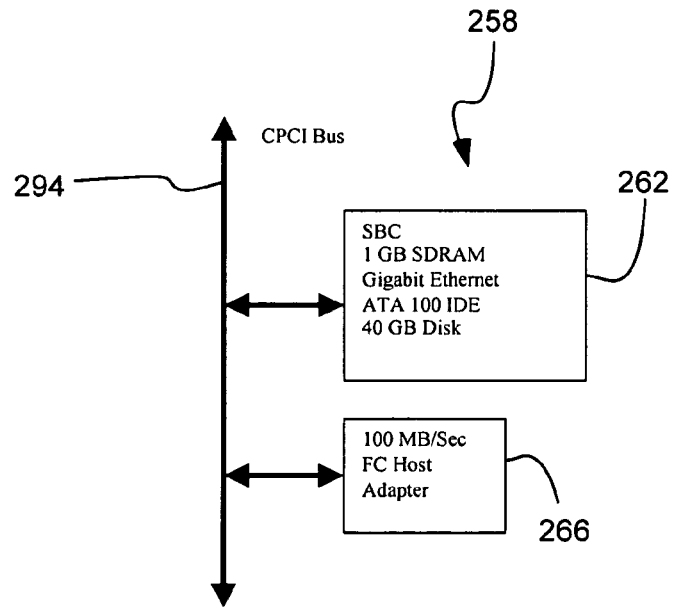
Figure 12C:
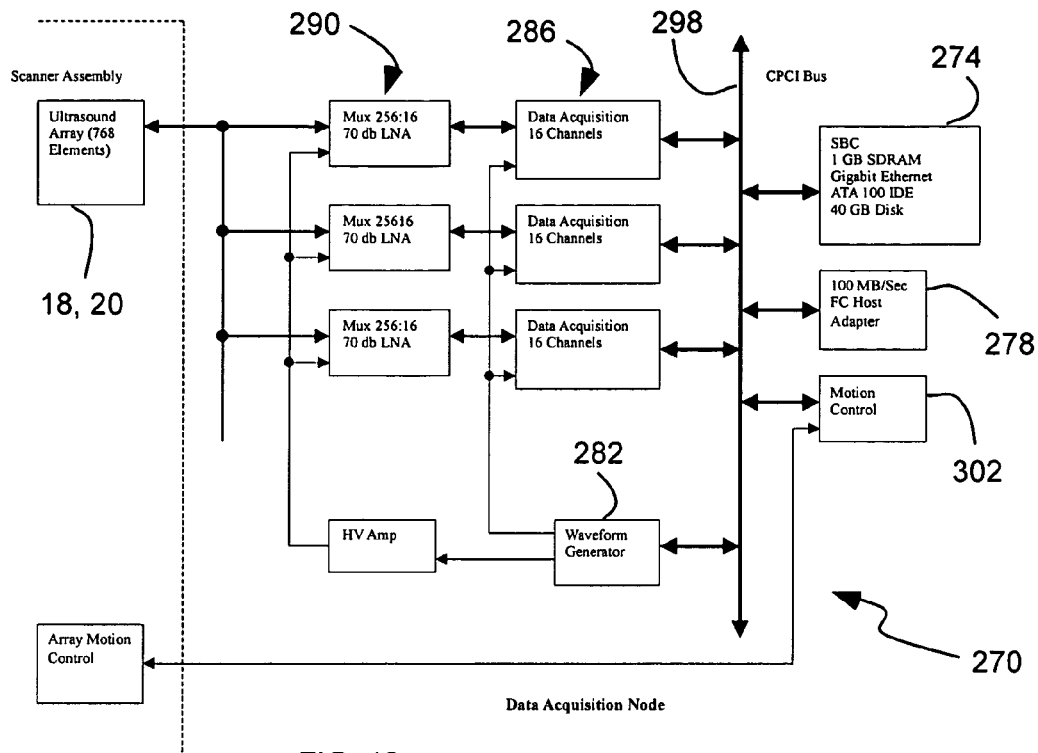
Figure 12D:
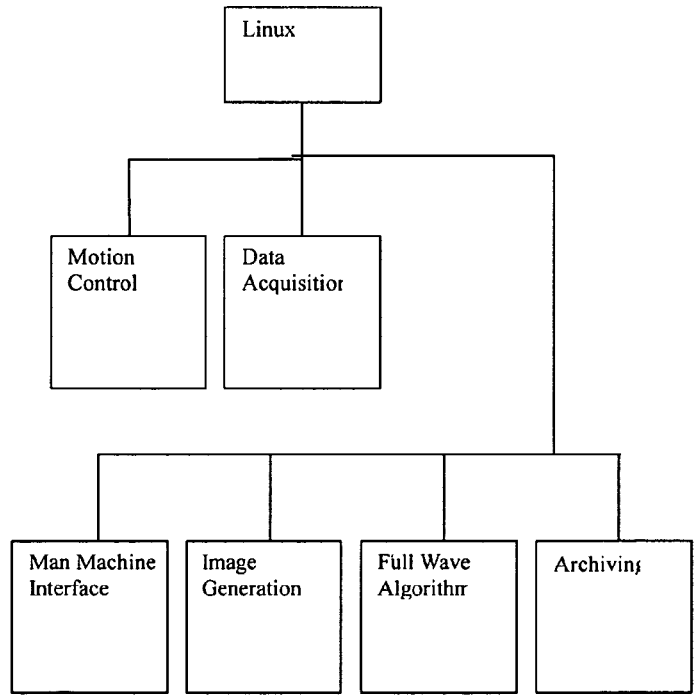

The system software block diagram is shown in FIG. 12d.

The architecture is configured to funnel data rapidly to RAID arrays. The RAID arrays are available to both store data and process data. Thus, data can be processed from a first slice, or data from the first slice can be accessed for computation, while storing data from the second slice. The architecture provides for an efficient exam. For example, a technician can review the data or generated images while the system is scanning. In addition, the data or images can be provided to a doctor immediately after the exam. Furthermore, the architecture reduces the size and cost of the computing components.

A method for using the system described above, and for scanning a breast, includes preconditioning the liquid or water in the preconditioning tank 80. The water can be introduced into the tank 80 from the water source 84. Before the water enters the tank 80 it can be filtered and de-ionized. The pressure of the water source can force the water into the tank. Alternatively, a pump can be used to pump water into the tank. The manual valve 90 can be opened to allow water to flow into the tank, while the check valve 88 resists water from flowing back to the water source. In addition, the system can control and open the electric valve 92 to allow water into the tank. The level sensor 94 can sense the level in the tank and is used to shut off the electric valve when the tank is full.

The water in the tank can be heated to a predetermined temperature with the heater 102. The thermocouple 104 can be used to determine the temperature and control the heater to maintain the desired temperature. Alternatively, the water can be separately preheated, such as by a water heater.

In addition, the water in the tank can be degassed with the degasser 108. The pump 112 can re-circulate the water through the circulation circuit 110, and through the orifice 116, creating a pressure differential that causes the gas released in the partial vacuum in the water to rise to the surface.

Furthermore, a predetermined amount of anti-bacterial and/or anti-viral agent, such as chlorine, can be introduced into the tank from the reservoir 120 by the metering pump 122.

The water can be preconditioned while the system is being used, or while a patient's breast is being scanned in the bath. After the water has been preconditioned, it can be transferred from the tank 80 to the bath 14 with the inlet pump 98. The flow can be controlled by the system through an electronic valve. The bath 14 can be filled until the water overflows the upper edge 132 and into the channel 134 or spillway. The sensor 138 can sense the water and shut off the pump 98 and close the valve. Alternatively, the motor can maintain a small trickle of water into the bath. The temperature of the water in the bath can be maintaining at the predetermined temperature (approximately 30° C.) by the heating element 126. In addition, the temperature of the water is stabilized.

The patient can be prepped while the water is being conditioned. A method for preparing a breast of a patient for scanning can include cleaning and drying a portion of the breast, such as the nipple. The breast magnet 160 can be secured to the breast with the breast connector 168. A table insert 52 can be selected from a plurality of table inserts having different sized apertures, and inserted into the table. In addition, an area of interest can be identified and marked on the breast.

The patient can be positioned on the horizontal table 38. The table can be initially positioned at the lowered position, and raised after the patient is on the table. The table can then be raised. Thus, the table can be initially raised to a higher elevation and subsequently lowered to a lower position. The breast can be disposed through the aperture 42 in the table. The gap between the table and the bath in the raised position allows the technician to center and pull the breast through the aperture. The table 38 can be displaced linearly vertically towards the bath to immerse the breast into the water. As the table is lowered, the upper edge 132 of the bath 14 can be received into the counter-bore 66 in the table.

After the breast is immersed in the bath, the breast is secured within the bath. The rod 176 can be raised until the bath magnet 164 docks with, or magnetically couples to, the breast magnet 160. The beveled cup 172 can assist in centering the magnets, and thus the breast. In addition, the rod 176 and the bath magnet 164 can be lowered to pull on and exert a degree of tension to the breast. Alternatively, the bath magnet can be coupled to the breast magnet prior to the breast being immersed within the bath. Thus, the table and rod can be lowered together into the bath. A length of the breast can be determined based on the position of the rod and the position of the table.

The arrays can be positioned so that a beam of light from the laser pointer 182 is projected onto the breast at the mark corresponding to the area of interest to be scanned. The position of the arrays can be determined by the system so that the system or technician can determine what portion of the breast to scan. The arrays can be raised or lowered a predetermined amount in order to scan the entire area of interest. Similarly, arrays can be positioned so that the cross-hairs associated with the camera 184 align with the mark.

The table can be lowered, and the arrays can be raised or positioned, by the technician visually observing the bath, arrays, table and breast, and controlling the table and/or arrays with a handheld control 190. The handheld control 190 allows the technician to move about and around the tank as necessary. The handheld control 190 can be wired to the system, as shown, or can be wireless. Alternatively, the table can be lowered, and the arrays can be raised or positioned, by the technician visually observing a display 194 operatively coupled to the camera 184. The display 194 can be a monitor of a terminal 198, such as a personal computer or the like. The handheld control and the terminal are examples of user interfaces that can be used to control the system.

The arrays 18 and 20 and the armature 24 can initially be in a lowered position. The arrays and armature can be raised and the breast scanned with ultrasound signals from the transducer arrays. As described above, the arrays can send and receive ultrasound signals at a plurality of elevational locations along the breast, and at a plurality of rotational orientations around the breast at each elevational location. Thus, the transducers can be sequentially moved through a plurality of different elevational locations along the breast. In addition, the transducers arrays can be sequentially moved through a plurality of different angular orientations around the breast at each elevational location.

The system or arrays can perform an initially, more rapid (or less detailed) scan of a larger length of the breast. Such an initial scan can be used to identify the area of interest in the breast. Then, the system can perform a subsequent, more slow or detailed scan of a smaller length of the breast around the area of interest.

The system can rapidly save data acquired from the transducer arrays, and save the data, such as in RAID arrays. The stored data can be simultaneously computed.

Referring again to FIGS. 1-4, the system 10 can include various other components, including for example, a power source (220 volts) 202, a high voltage source (120 volts) 204 for pumps and the like, a low voltage source (24 volts) for sensors and control valve and the like, computer(s) and drive array(s) such as the CompactPCI(s) chassis 210, etc. Many or all of the various components can be housed or contained in the base 34 or frame so that the system can be compact and self contained. The terminal 198 can be coupled to the computers and/or other components in the base by standard connections. The terminal 198 can be remote from the base, as shown, or can be coupled thereto.

It is to be understood that the above-referenced arrangements are illustrative of the application for the principles of the present invention. It will be apparent to those of ordinary skill in the art that numerous modifications can be made without departing from the principles and concepts of the invention as set forth in the claims.

What is claimed is:

1. A breast scanning system configured to scan a breast of a patient, comprising:
   a) a bath containing a medium;
   b) transducer arrays, disposable in the bath, configured to transmit and receive ultrasound signals;
   c) a horizontal table, disposable over the bath, with the patient thereon, having an aperture formed in the table and positionable over the bath with the breast of the patient pendent therethrough; and
   d) the table and the bath being linearly vertically displaceable with respect to one another between 1) a lowered position where the table is adjacent the bath with the breast within the bath, and 2) a raised position where the table is spaced-above the bath with the breast elevated above the medium of the bath; and e) means for maintaining the table in the raised position with the table spaced-above the bath.

2. A device in accordance with claim 1, wherein the means for maintaining the table further comprises:
at least one column supporting the table.

3. A device in accordance with claim 2, wherein the means for maintaining the table further comprises:
a motor, coupled to the at least one column, to raise and lower the at least one column, and thus the table.

4. A device in accordance with claim 1, further comprising:
a plurality of table inserts, each insertable into the table and each having a different sized aperture formed therein.

5. A device in accordance with claim 1, further comprising:
an annular projection, formed around the aperture in the table, and extending beyond a lower surface of the table.

6. A device in accordance with claim 1, further comprising:
a chamfer, bevel or radius formed in the table around the aperture.

7. A device in accordance with claim 1, further comprising:
a counter-bore, formed in a lower surface of the table around the aperture, sized to receive an upper portion of the bath when the table is in the lowered position.

8. A device in accordance with claim 1, wherein the medium includes a liquid; and further comprising:
a preconditioning tank, fluidly coupled to the bath, configured to precondition the liquid prior to being introduced into the bath; and
means for transferring liquid from the preconditioning tank to the bath.

9. A device in accordance with claim 8, further comprising:
a heater, coupled to the preconditioning tank; and
a thermocouple, associated with the preconditioning tank and operatively coupled to the heater.

10. A device in accordance with claim 8, further comprising:
a de-gaser, coupled to the preconditioning tank.

11. A device in accordance with claim 8, wherein the de-gaser further includes:
a recirculation pump, coupled to the preconditioning tank in a circulation circuit to pump liquid from the preconditioning tank back into the preconditioning tank; and
at least one orifice, disposed in the circulation circuit having a diameter less than a diameter of the circulation circuit, and configured to introduce a pressure differential across the at least one orifice.

12. A device in accordance with claim 8, further comprising:
a de-ionizer, coupled to a liquid supply line to the preconditioning tank.

13. A device in accordance with claim 8, further comprising:
a reservoir, fluidly coupled to the preconditioning tank, configured to contain an antibacterial or antiviral agent; and
a metering pump, coupled between the reservoir and the preconditioning tank.

14. A device in accordance with claim 1, wherein the medium includes a liquid; and further comprising:
a heater, associated with the bath, and configured to maintain a desired temperature of the liquid within the bath; and
a thermocouple, associated with the bath and operatively coupled to the heater.

15. A device in accordance with claim 1, further comprising:
an annular channel, disposed around an upper edge of the bath.

16. A device in accordance with claim 15, further comprising:
a liquid sensor, disposed in the channel.

17. A device in accordance with claim 1, further comprising:
a seal, compressible between the bath and the table in the lowered position.

18. A device in accordance with claim 1, further comprising:
a pinch sensor, disposed between the bath and the table.

19. A device in accordance with claim 1, further comprising:
means for securing the breast within the bath.

20. A device in accordance with claim 1, further comprising a breast retention assembly including:
a breast magnet with a breast connector configured to secure the breast magnet to the breast of the patient; and
a bath magnet, disposed in the bath and magnetically coupleable to the breast magnet when the table is in the lowered position.

21. A device in accordance with claim 20, wherein the breast retention assembly further comprises:
a beveled cup, associated with one of the breast or bath magnets, to center the breast or bath magnets.

22. A device in accordance with claim 20, further comprising:
a rod, attached to the bath magnet and vertically movable within the bath.

23. A device in accordance with claim 1, further comprising:
a laser pointer, associated with the bath, configured to project a light beam onto the breast at an area of interest.

24. A device in accordance with claim 1, further comprising:
a camera, associated with the bath, configured to provide an image of the breast.

25. A device in accordance with claim 1, further comprising:
an armature, disposable in the bath and carrying the transducer arrays;
a rotational motor, coupled to the armature, to rotate the armature, and thus the transducer arrays; and
a linear motor, coupled to the armature, to linearly displace the armature, and thus the transducer arrays.

26. A device in accordance with claim 1, wherein the table and the bath are horizontally displaceable with respect to one another between 1) a scan position in which the table is disposed over the bath; and 2) a non-scan position in which the aperture is disposable horizontally spaced-apart from the bath.

27. A device in accordance with claim 1, further comprising:
a drain pump, coupled to a drain in the bath.

28. A device in accordance with claim 1, further comprising:
a plurality of interconnected nodes, coupled to the transducer arrays, including at least one compute node and at least one data acquisition node;
the at least one compute node including a single board computer and a fibre channel host adaptor; and the at least one data acquisition node including a single board computer, a fibre channel host adaptor, a waveform generator card, a data acquisition card, and a Mux card.

29. A device in accordance with claim 1, wherein the bath is disposed on and supported by a base; wherein the transducer arrays are movably disposed in the bath; wherein the table is carried by the base; and wherein the table is linearly vertically displaceable with respect to the bath and the base.

30. A breast scanning system configured to scan a breast of a patient, comprising:
   a) a bath configured to contain a medium;
   b) transducer arrays, disposable in the bath, configured to transmit and receive ultrasound signals;
   c) a table, disposable over the bath, the table and bath being linearly vertically displaceable with respect with one another, configured to receive the patient thereon, having an aperture formed in the table and positionable over the bath configured to receive the breast of the patient pendent therethrough; and
   d) means for securing the breast within the bath, including:
      a breast magnet with a breast connector configured to secure the breast magnet to the breast of the patient;
      a bath magnet disposed in the bath and magnetically coupleable to the breast magnet when the table is in the lowered position, and
      a rod attached to the bath magnet and vertically movable within the bath.

31. A device in accordance with claim 30, further comprising:
   a beveled cup, associated with one of the breast or bath magnets, to center the breast or bath magnets.

32. A device in accordance with claim 30, further comprising:
   an armature, disposable in the bath and carrying the transducer arrays; and
   the rod extending through the armature.

33. A device in accordance with claim 30, further comprising:
   the table and the bath being linearly vertically displaceable with respect to one another between 1) a lowered position where the table is adjacent the bath configured to position the breast within the bath, and 2) a raised position where the table is spaced-above the bath configured to elevate the breast above the bath; and
   means for maintaining the table in the raised position with the table spaced-above the bath.

34. A breast scanning system configured to scan a breast of a patient, comprising:
   a) a bath configured to contain a medium;
   b) transducer arrays, disposable in the bath, configured to transmit and receive ultrasound signals;
   c) a table, disposable over the bath, the table and bath being linearly vertically displaceable with respect with one another, configured to receive the patient thereon, having an aperture and a cavity formed in the table and positionable over the bath configured to receive the breast of the patient pendent therethrough; and
   d) a plurality of table inserts, each insertable into the cavity of the table to be flush with the table, and each having a different sized aperture formed therein.

35. A device in accordance with claim 34, further comprising:
   an annular projection, formed around the aperture in the table, and extending beyond a lower surface of the table.

36. A device in accordance with claim 34, further comprising:
   a counter-bore, formed in a lower surface of the table around the aperture, sized to receive an upper portion of the bath when the table is in the lowered position.

37. A device in accordance with claim 34, further comprising:
   the table and the bath being linearly vertically displaceable with respect to one another between 1) a lowered position where the table is adjacent the bath configured to position the breast within the bath, and 2) a raised position where the table is spaced-above the bath configured to elevate the breast above the bath; and
   means for maintaining the table in the raised position with the table spaced-above the bath.

38. A breast scanning system configured to scan a breast of a patient, comprising:
   a) a bath configured to contain a medium;
   b) transducer arrays, disposable in the bath, configured to transmit and receive ultrasound signals;
   c) a table, disposable over the bath, the table and bath being linearly vertically displaceable with respect with one another, configured to receive the patient thereon, having an aperture formed in the table and positionable over the bath configured to receive the breast of the patient pendent therethrough; and
   d) an annular projection, formed around the aperture in the table, and extending beyond a lower surface of the table.

39. A device in accordance with claim 38, further comprising:
   a plurality of table inserts, each insertable into the table and each having a different sized aperture formed therein.

40. A device in accordance with claim 38, further comprising:
   a counter-bore, formed in the lower surface of the table around the aperture, sized to receive an upper portion of the bath when the table is in the lowered position.

41. A device in accordance with claim 38, further comprising:
   the table and the bath being linearly vertically displaceable with respect to one another between 1) a lowered position where the table is adjacent the bath configured to position the breast within the bath, and 2) a raised position where the table is spaced-above the bath configured to elevate the breast above the bath; and
   means for maintaining the table in the raised position with the table spaced-above the bath.

42. A breast scanning system configured to scan a breast of a patient, comprising:
   a) a bath configured to contain a medium;
   b) transducer arrays, disposable in the bath, configured to transmit and receive ultrasound signals;
   c) a table, disposable over the bath, the table and bath being linearly vertically displaceable with respect with one another, configured to receive the patient thereon, having an aperture formed in the table and positionable over the bath configured to receive the breast of the patient pendent therethrough; and
   d) a counter-bore, formed in a lower surface of the table around the aperture, sized to receive an upper portion of the bath when the table is in the lowered position.

43. A device in accordance with claim 42, further comprising:
   an annular projection, formed around the aperture in the table, and extending beyond the lower surface of the table.

44. A device in accordance with claim 42, further comprising:
a plurality of table inserts, each insertable into the table and each having a different sized aperture formed therein.

45. A device in accordance with claim 42, further comprising:
the table and the bath being linearly vertically displaceable with respect to one another between 1) a lowered position where the table is adjacent the bath configured to position the breast within the bath, and 2) a raised position where the table is spaced-above the bath configured to elevate the breast above the bath; and
means for maintaining the table in the raised position with the table spaced-above the bath.

46. A breast scanning system configured to scan a breast of a patient, comprising:
a) a bath configured to contain a liquid;
b) transducer arrays, disposable in the bath, configured to transmit and receive ultrasound signals;
c) a table, disposable over the bath, the table and bath being linearly vertically displaceable with respect with one another, configured to receive the patient thereon, having an aperture formed in the table and positionable over the bath configured to receive the breast of the patient pendent therethrough;
d) an annular channel, disposed around an upper edge of the bath; and
e) a seal, compressible between the bath and the table in the lowered position.

47. A device in accordance with claim 46, further comprising:
a liquid sensor, disposed in the channel.

48. A device in accordance with claim 46, further comprising:
a pinch sensor, disposed between the bath and the table.

49. A device in accordance with claim 46, further comprising:
the table and the bath being linearly vertically displaceable with respect to one another between 1) a lowered position where the table is adjacent the bath configured to position the breast within the bath, and 2) a raised position where the table is spaced-above the bath configured to elevate the breast above the bath; and
means for maintaining the table in the raised position with the table spaced-above the bath.

50. A method for preparing a breast of a patient for scanning, comprising the steps of:
a) positioning the patient on a horizontal table;
b) disposing the breast through an aperture in the table;
c) linearly vertically displacing the table and a bath of medium with respect to one another by initially raising the table to a higher elevation and subsequently lowering the table to a lowered position adjacent the bath prior to scanning the breast to immerse the breast into the medium; and
d) scanning the breast with ultrasound signals from transducer arrays.

51. A method in accordance with claim 50, wherein the step of disposing the breast through the aperture further includes:
selecting a table insert from a plurality of table inserts having different sized apertures; and
inserting the table insert into the table.

52. A method in accordance with claim 50, wherein the step of displacing the table further includes:
receiving an upper edge of the bath into a counter-bore in a lower surface of the table.

53. A method in accordance with claim 50, further comprising the step of:
projecting a beam of light onto the breast to identify an area of interest to be scanned.

54. A method in accordance with claim 50, further comprising the step of:
viewing an image of the breast including an area of interest to be scanned.

55. A method in accordance with claim 50, wherein the step of scanning further includes:
sending and receiving ultra sound signals at a plurality of elevational locations along the breast, and at a plurality of rotational orientations around the breast at each elevational location.

56. A method in accordance with claim 50, wherein the step of scanning further includes:
sequentially moving transducer arrays through a plurality of different elevational locations along the breast; and
sequentially moving the transducer arrays through a plurality of different angular orientations around the breast at each elevational location.

57. A method in accordance with claim 50, further comprising the steps of:
a) preconditioning a liquid in a tank; and
b) transferring the liquid from the tank to a bath.

58. A method in accordance with claim 50, further comprising the steps of:
storing data acquired by the transducer arrays; and
simultaneously performing computations with stored data.

59. A method for preparing a breast of a patient for scanning, comprising the steps of:
a) securing a breast magnet to the breast;
b) positioning the patient on a table positioned over a bath containing a medium, the table and bath being linearly vertically displaceable with respect with one another;
c) disposing the breast through an aperture in the table;
d) securing the breast within the bath; and
e) scanning the breast with transducer arrays.

60. A method in accordance with claim 59, wherein the step of securing the breast further includes:
coupling the breast magnet on the breast to a bath magnet in a bath.

61. A method in accordance with claim 60, wherein the breast is immersed within the bath prior to the bath magnet being coupled to the breast magnet.

62. A method in accordance with claim 59, wherein bath magnet is coupled to the breast magnet prior to the breast being immersed within the bath.

63. A method in accordance with claim 59, further comprising the step of:
pulling on the bath magnet coupled to the breast magnet to tension the breast.

64. A method in accordance with claim 59, wherein the step of coupling the breast magnet on the breast to the bath magnet in the bath further includes:
lowering the breast into the bath;
raising a rod with the bath magnet thereon until the breast and bath magnets magnetically engage one another; and
slightly lowering the rod to tension the breast.

65. A method in accordance with claim 64, wherein a length of the breast is determined based on a position of the rod and a position of the table.

66. A method for preparing a breast of a patient for scanning, comprising the steps of:
a) positioning the patient on a table positioned over a bath containing a medium, the table and bath being linearly vertically displaceable with respect with one another;

b) disposing the breast through an aperture in the table;

c) immersing the breast into medium in a the bath;

d) initially more rapidly scanning a larger length of the breast with ultrasound signals from transducer arrays to identify an area of interest in the breast; and e) subsequently more slowly scanning a smaller length of the breast around the area of interest with ultrasound signals from the transducer arrays.

67. A breast scanning system configured to scan a breast of a patient, comprising:

a) a bath configured to contain a medium;

b) transducer arrays, disposable in the bath, configured to transmit and receive ultrasound signals;

c) a horizontal table, disposable over the bath, configured to receive the patient thereon, having an aperture formed in the table and positionable over the bath configured to receive the breast of the patient pendent therethrough;

d) the table and the bath being linearly vertically displaceable with respect to one another between 1) a lowered position where the table is adjacent the bath configured to position the breast within the bath, and 2) a raised position where the table is spaced-above the bath configured to elevate the breast above the bath;

e) means for maintaining the table in the raised position with the table spaced-above the bath; and f) a breast retention assembly including:

a breast magnet with a breast connector configured to secure the breast magnet to the breast of the patient;

a bath magnet, disposed in the bath and magnetically coupleable to the breast magnet when the table is in the lowered position; and a rod, attached to the bath magnet and vertically movable within the bath.

68. A device in accordance with claim 67, further comprising:

a beveled cup, associated with one of the breast or bath magnets, to center the breast or bath magnets.

69. A device in accordance with claim 67, further comprising:

an armature, disposable in the bath and carrying the transducer arrays; and the rod extending through the armature.

70. A device in accordance with claim 67, further comprising:

the table and the bath being linearly vertically displaceable with respect to one another between 1) a lowered position where the table is adjacent the bath configured to position the breast within the bath, and 2) a raised position where the table is spaced-above the bath configured to elevate the breast above the bath; and means for maintaining the table in the raised position with the table spaced-above the bath.

\* \* \* \* \*